United States Patent [19]
Bowman et al.

[11] Patent Number: 5,559,264
[45] Date of Patent: Sep. 24, 1996

[54] PROCESS FOR MAKING CHLOROORGANOSILICON COMPOUNDS

[75] Inventors: Mark P. Bowman; Curtis L. Schilling, Jr., both of Marietta, Ohio

[73] Assignee: OSi Specialities, Inc., Danbury, Conn.

[21] Appl. No.: 389,081

[22] Filed: Feb. 14, 1995

Related U.S. Application Data

[63] Continuation of Ser. No. 202,192, Feb. 24, 1994, abandoned.
[51] Int. Cl.$^6$ .................................................. C07F 7/08
[52] U.S. Cl. .................................................. 556/479
[58] Field of Search ........................................ 556/479

[56] References Cited

U.S. PATENT DOCUMENTS

| | | |
|---|---|---|
| 3,795,656 | 3/1974 | Martin . |
| 4,039,567 | 8/1977 | Kötzsch et al. . |
| 4,224,233 | 9/1980 | Seiler et al. . |
| 4,533,744 | 8/1985 | Williams, Jr. . |
| 4,584,395 | 4/1986 | Panster et al. . |
| 4,614,812 | 9/1986 | Schilling, Jr. . |
| 4,658,050 | 4/1987 | Quirk et al. . |
| 5,177,236 | 1/1993 | Seiler et al. . |
| 5,248,802 | 9/1993 | Bank ................... 556/479 X |
| 5,312,945 | 5/1994 | Bank ................... 556/479 X |

FOREIGN PATENT DOCUMENTS

| | | |
|---|---|---|
| 0403706A3 | 9/1989 | European Pat. Off. . |
| 6-157555 | 6/1994 | Japan . |
| 111276 | 11/1979 | Poland . |

OTHER PUBLICATIONS

Svoboda, et al., "Catalysis by Metal Complexes", *Collection Czechoslov. Chem. Commun.*, 38:1235–1241 (1973).
Hilal, et al., "Cluster versus Non–Cluster Catelysis in Olefin Thermal Isomerization and Hydrosilylation in the Presence of $Ru_3(CO)_{12}$," *J. Organometallic Chemistry*, 452:167–173 (1993).
Marciniec, et al., "Catalysis of Hydrosilation", *J. Organometallic Chemistry*, 253:349–362 (1983).
Tanaka, et al., "Ruthenium Complex–Catalyzed Hydrosilylation of Allyl Chloride with Trimethoxysilane", *J. Molecular Catalysis*, 81:207–214 (1993).
Cabeza, et al., "Reactivity of Tertiary Silanes and Stannanes With an Edge–Bridged Triruthenium Carbonyl Cluster Complex", *Inorg. Chem.*, 32:4640–4642 (1993).
Cabeza, et al., "Incorporation of Silanes and Diphenylacetylene Into Face–Bridged Triruthenium Carbonyl Clusters. Attempted Hydrosilylation of Diphenylacetylene", *Organometallics*, 12:2973–2979 (1993).

Seki, et al., "The Synthesis of (E)–1,2–disilylethenes From a Triorganosilylethene With the Aid of $Ru_3(CO)_{12}$ and a Hydrosilane", *J. Organometallic Chemistry*, 369:117–123 (1989).
Svoboda, et al., "Reactions of $[(C_6H_5)_3P]_3RuCl_2$ With Some Silicon Hydrides", *Collection Czechoslov. Chem. Commun.*, 39:1324–1329 (1974).
Belyakova, et al., "Patterns of Behavior in the Reactions of Hydride Silanes with Allyl Chloride", translated from *Ahurnal Obschei Khimii*, 44(11):2439–2442 (1974).
Deschler, et al., "3–Chloropropyltrialkoxysilanes–Key Intermediates for the Commercial Production of Organofunctionalized Silanes and Polysiloxanes", *Angew. Chem. Int. Ed. Engl.*, 25:236–252 (1986).
*Comprehensive Handbook on Hydrosilylation*, B. Marciniec, Pergamon Press, pp. 69–74, 372, 421, 455, 558 (1992).
Marciniec et al., "Catalysis of Hydrosilylation, Part II. Addition of Trialkoxysilanes to Vinyltrialkoxysilanes Catalyzed by Transition Metal Complexes", *Polish Journal of Chemistry* 56:287–296 (1982).
Marciniec et al., "Effect of Substituents on Silicon on Cross–Metathesis of Vinylsilanes with 1–Alkenes in the Presence of Ruthenium Complexes", *Journal of Molecular Catalysis*, 76:307–317 (1992).
Seiki et al., "Single–Operation Synthesis of Vinylsilanes from Alkenes and Hydrosilanes With the Aid of $Ru_3(CO)_{12}$", *Journal of Organic Chemistry*, 51(20):3890–3895 (1986).
Marciniec et al., "Ruthenium Phosphine Complexes as Catalysts for the Hydrosilylation of the C═C Bond", *Journal of Molecular Catalysis*, 10:123–126 (1981).
Esteruelas et al., "Exclusive Formation of cis–PhDH═CH(SiEt$_3$ ) by Addition of HSiEt$_3$ to PhC≡CH Catalyzed by RuHCl(CO)(PiPr$_3$)$_2$", *Organometallics*, 12:2377–2379 (1993).
Ojima et al., "The Reaction of Hydrosilances with Trifluoropropene and Pentafluorostyrene, Catalyzed by Ruthenium, Rhodium and Palladium Complexes", *Journal of Organometallic Chemistry*, 260:335–346 (1984).
*Chemical Abstracts*, 98:4661n (1983)—Japan 57/109,795.
*Chemical Abstracts*, 98:72425p (1983)—Japan 57/140,788.
Nishino et al., "Preparation of (halopropyl)alkoxysilances", *Chem. Abst.*, 121:1124 (1994) Abstract 121:109253c.
*Chemical Abstracts*, 122:81617u (1995)—JP 06–157,555.

*Primary Examiner*—Paul F. Shaver
*Attorney, Agent, or Firm*—Banner & Allegretti, Ltd.

[57] ABSTRACT

A method for preparing chloroalkylalkoxysilanes by reacting an allylic chloride with a small molar excess of a hydromethoxysilane in the presence of a ruthenium catalyst and preferably in the substantial absence of an inert solvent.

38 Claims, No Drawings

PROCESS FOR MAKING CHLOROORGANOSILICON COMPOUNDS

This application is a continuation of application Ser. No. 08/202,192, filed Feb. 24, 1994, now abandoned.

FIELD OF THE INVENTION

The present invention relates to a method of preparing certain chloroorganosilicon compounds. More particularly, the invention relates to a process for directly hydrosilating allyl chloride or methallyl chloride with a hydromethoxysilane.

BACKGROUND OF THE INVENTION

Chloroorganosilicon compounds have long been articles of commerce. Such materials are useful in a variety of known applications or as intermediates in the preparation of other organofunctional silicon compounds. Such other organofunctional silicon compounds are prepared by replacing chlorine atoms, in chloroorganic groups attached to silicon atoms in such compounds, with functional groups including those derived from ammonia and its organic derivatives, hydrogen sulfide and its organic derivatives, oligomers of sulfur, carboxylic acid groups including methacrylate groups, and substituted phenoxide groups, among others. The versatility of chloroorganosilicon compounds as intermediates in preparing such organofunctional silicon compounds has contributed to their commercial success in spite of major recognized deficiencies associated with the processes for preparing such chloroorganosilicon compounds.

Thus, since their commercial introduction, there has been an ongoing need in the art to prepare such chloroorganosilicon compounds safely in high yields and efficiencies, with reduced raw material costs, including catalyst costs, and with reduced generation of hard-to-dispose waste by-products.

Current large scale commercial production of such chloroorganosilicon compounds is based on a two-step procedure. In the first step, platinum is used to catalyze a reaction between a hydrosilicon compound, specifically a hydrochlorosilane, and an olefinic chloroorganic compound, specifically allyl chloride or methallyl chloride. This hydrosilation reaction yields a chloroorganochlorosilane, which then must be converted in a second step to the corresponding chloroorganoalkoxysilane or chloroorganosiloxane by methods known in the art.

From a commercial perspective, these hydrosilation reactions suffer from several recognized deficiencies. First, yields in the platinum-catalyzed hydrosilation of allyl chloride, calculated on a molar basis from the limiting reactant, do not exceed 83%. Second, platinum-containing hydrosilation catalysts are very expensive. Third, while the platinum-catalyzed hydrosilation of methallyl chloride with a hydrochlorosilane occurs in higher yield than with allyl chloride, the higher cost of methallyl chloride both on a combined per unit weight and molecular weight basis does not justify its use. Fourth, a second process step is necessary to convert the chloroorganochlorosilane to a chloroorganoalkoxysilane for subsequent use. Even though the product of the first step process, e.g., a chloropropylchlorosilane, can be converted in the second step to the corresponding chloropropylalkoxysilane in high yield, the overall yield from the two-step process still suffers from the modest yield in the first step. Also, none of the chlorine present in the hydrochlorosilane raw material ends up in the final product. It must either be recycled to trichlorosilane via its direct synthesis or to methyl chloride for the direct synthesis of methylchlorosilanes, or it must be destroyed as waste, adding to process cost and complexity.

While there have been recent improvements in yields and efficiencies for platinum-catalyzed hydrosilation reactions between allyl chloride and trichlorosilane or methyldichlorosilane, the results remain disappointing. Such improvements have dealt primarily with the use of various forms of reusable platinum catalysts, to reduce catalyst costs, or with venting by-product propylene, to increase conversion of the hydrochlorosilane raw material to the desired product.

Similar yields and efficiencies also have been reported for the iridium complex-catalyzed direct hydrosilation of allyl chloride with trimethoxysilane. For example, a yield of 78.4% of chloropropyltrimethoxysilane on a molar basis has been reported for the equimolar reaction of trimethoxysilane and allyl chloride using an iridium-cyclooctene complex as the hydrosilation catalyst (Tanaka et al, *Journal of Molecular Catalysis*, 81 (1993): 207–214). While the reported yield suggests that an incremental improvement over state-of-the-art commercial processes is possible, the cost of iridium is higher than that of platinum. Given that the iridium use level was nearly 672 parts per million by weight of total reaction charge, the catalyst cost is much too high for the process to be of much commercial interest at the present time.

The same researchers also report the results of directly hydrosilating allyl chloride with trimethoxysilane in the presence of several ruthenium complexes. A maximum yield of 73.6% of chloropropyltrimethoxysilane is reported in Table 2 for the reaction between trimethoxysilane and allyl chloride at a 4/1 molar ratio. Assuming the use of the "typical reaction procedure," the process may have employed a ruthenium carbonyl catalyst in an amount to provide at least about 155 parts per million by weight of ruthenium metal in the reaction mixture. Apparently, the reaction also was conducted in a sealed reactor under autogenous pressure in the presence of at least 13.3% by weight of toluene solvent for 16 hours at 80° C. The conversion of limiting allyl chloride was complete, and thus the yields of by-products such as propyltrimethoxysilane, tetramethoxysilane and hydrogen, were not insignificant. The same reaction, at a 2/1 molar ratio of trimethoxysilane to allyl chloride, in the presence of the same absolute weights of ruthenium catalyst and toluene solvent, provided a 72.2% yield of chloropropyltrimethoxysilane on a molar basis, with similar by-product yields at complete conversion of limiting allyl chloride. At a 1/1 molar ratio, the conversion of allyl chloride was not complete. At this mole ratio, a maximum yield of only 52.4% was obtained after 16 hours at 50° C., while at 80° C. the yield was only 26.4%. (Table 2).

Thus, while equivalent molar yields of the desired chloropropyltrimethoxysilane were obtained at peak operation relative to other prior art methods using platinum and iridium catalysts, the yields per unit volume of equipment were necessarily low, due to the use of solvent and to the use of large excesses of trimethoxysilane.

Marciniec et al, *Journal of Organometallic Chemistry*, 253 (1983): 349–362, also reports ruthenium compound-catalyzed hydrosilation of C=C bonds. In the case of hydroalkoxysilanes, the reaction is said to proceed only in the absence of solvent and in the case of certain catalysts, is enhanced by oxygen. The authors had essentially no success, however, hydrosilating substituted olefins, including allyl compounds.

Yields from the above-reported ruthenium-catalyzed hydrosilation reactions between trimethoxysilane and allyl chloride, although modest, are interesting in view of the use of ruthenium compounds to catalyze other reactions from similar reactants. Formation of undesired, unsaturated by-products is known to occur, at times to a significant extent, in ruthenium-catalyzed reactions of certain hydrosilicon compounds with olefins. Such other reactions include dehydrocondensation reactions wherein hydrosilicon compounds and olefins react to form vinylic silicon derivatives, olefin metathesis reactions wherein two olefins react to form two different olefins, olefin reduction, and olefin isomerization. These other reactions are noted on occasion to occur with the total exclusion of hydrosilation. Surprisingly, the formation of such by-products does not occur to any significant extent in the process of the present invention.

In contrast to the above reported hydrosilation reactions of allyl chloride and of the propensity of ruthenium compounds to catalyze a variety of reactions between hydrosilicon compounds and olefins, the process of the present invention provides chloropropylmethoxysilanes in nearly quantitative yields based on limiting allyl chloride when trimethoxysilane is used. The process of the present invention uses a relatively low molar excess of the hydromethoxysilane, and can operate with a much lower level of the ruthenium catalyst, and with shorter reaction times. The process produces low levels of waste by-products, and can substantially eliminate any need for a solvent, while reducing limitations on the equipment which may be used.

SUMMARY OF THE INVENTION

The present invention provides a method of preparing chloroorganosilicon compounds and in particular chloropropyltrimethoxysilane and other closely related chloroalkylalkoxysilanes. The method specifically involves reacting an allylic chloride with a small molar excess of a hydromethoxysilane, preferably in the substantial absence of solvent, and in the presence of an effective amount of a ruthenium metal-containing catalyst according to the following general equation:

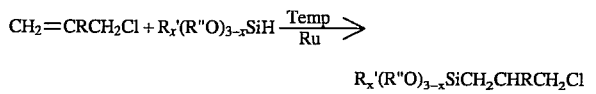

$$R_x'(R''O)_{3-x}SiCH_2CHRCH_2Cl$$

wherein x is 0, 1, or 2, R is H or a methyl group, R' is a methyl group, R" is R', Temp is temperature from ambient to 150° C., and Ru is a catalyst containing ruthenium metal in combined or elemental form, with the proviso that as the reaction temperature is increased, the concentration of the allylic chloride present in the reaction mixture is limited by its slow addition to a molar excess of hydromethoxysilane.

The process of the present invention can be performed in a variety of commercially available equipment now used for hydrosilation reactions, including equipment in which such reactions are performed in continuous fashion.

By integrating the present process with a source of trimethoxysilane, prepared directly from silicon metal and methanol, one can avoid the use of corrosive and hazardous hydrochlorosilanes and eliminate the generation of large amounts of chlorine-containing waste by-products which are inherent to the use of products derived from hydrochlorosilanes.

DETAILED DESCRIPTION OF THE INVENTION

It has surprisingly been discovered that several factors are important for obtaining high yields of chloroorganosilicon compounds from a one-step hydrosilation reaction between an allylic chloride and a hydromethoxysilane. First, when all reactants are combined at the start in a batch reaction, selectivity to the desired chloroorganosilane product is highest at lower temperatures and lower reaction rates. Second, when temperature is increased to improve reaction rates, selectivity surprisingly can be maintained by limiting the concentration of allylic chloride in the reaction mixture. Third, most inert solvents have a surprisingly negative effect on rates, selectivities, or both, particularly in a batch system and therefore should be excluded.

Preferably, the process is carried out by slowly adding the allylic chloride to a reactor containing hydromethoxysilane and reacting them in the presence of a ruthenium metal-containing catalyst in either a semi-batch or continuous process. This order of addition effectively maintains a minimum concentration of unreacted allylic chloride in the reaction medium relative to the hydromethoxysilane, and thus effectively establishes a very large molar excess of the hydromethoxysilane relative to the allylic chloride in the reaction medium. In general practice, the maximum rate of addition of the allylic chloride to the hydromethoxysilane will be determined by the reaction rate, which is dependent in part on the reaction temperature and the catalyst concentration, and by the heat transfer limitations of the reaction equipment, whether a small laboratory reactor or a very large commercial reactor is used, as will be understood by one skilled in the art.

The preferred order of combination can be achieved in semi-batch or continuous operation. In semi-batch operation, a reactor first is charged with a large portion of, and preferably with the full complement of, the molar excess of hydromethoxysilane. Thereafter, the allylic chloride is slowly added to the reactor and the allylic chloride and hydromethoxysilane are reacted in the presence of the ruthenium catalyst. As used herein, slow addition of allylic chloride generally means at a rate below about 3 moles of allylic chloride per hour per mole of hydromethoxysilane, and preferably at or below 1 mole per hour per mole of hydromethoxysilane. For example, in a semi-batch process, an addition rate of 2 moles of allylic chloride/hr/mole of hydromethoxysilane is practiced when 1 mole of allylic chloride is added to a reactor containing 2 moles of hydromethoxysilane in 15 minutes. Once the allylic chloride has been added to the reactor, the reaction is continued until complete conversion of the allylic chloride is obtained. While this, in large part, is a function of temperature and catalyst concentration, complete conversion generally can be achieved in 1 to 15 hours and more usually between 1 to 10 hours. Completion of the reaction in 1 to 5 hours is not unusual. Some portion of the hydromethoxysilane also can be added in admixture with the allylic chloride or simultaneously with the addition of the allylic chloride as a separate stream.

In continuous operation, the reactor typically is charged with separate streams of the allylic chloride and hydromethoxysilane at a mole ratio of hydromethoxysilane to allylic chloride between about 1.01:1 to 3:1, and preferably at a mole ratio between about 1.1:1 to 2:1. Such operation ensures a proper excess of hydromethoxysilane in the reaction vessel under steady state operating conditions.

Solvents which have been found to have a negative effect on hydrosilation rates, selectivities, or both, in at least certain instances include common aromatic hydrocarbon solvents, such as benzene, toluene, xylenes, cumene, other alkylated benzenes, and higher aromatics in alkylated or unalkylated form. While toluene degrades selectivity in a batch system, when the process is performed in accordance with the preferred embodiment by adding allyl chloride to the molar excess of hydromethoxysilane, the presence of toluene solvent has a reduced adverse impact on selectivity to the desired product. Selectivity can be maintained at or near the desired level at the expense of a lower reaction rate and a lower yield per unit volume of the equipment. Other solvents which have negative effects on rate, selectivity, or both, include alkanes such as hexane, nitriles such as acetonitrile, ethers such as isopropyl ether, haloalkanes such as dichloroethane, ketones such as acetone, and alcohols such as ethanol. Because the process of the invention is essentially quantitative and rapid under preferred operating conditions, further promotion of rates and enhancement of yields by using a solvent is unlikely. Thus, use of a solvent generally should be avoided.

As noted, the process of the present invention does not require and preferably avoids the use of inert solvents, since they generally have a negative effect on rate, selectivity, or both, and their use reduces the yield per unit volume of the production equipment. By avoiding any need for a solvent, the process of the present invention increases the effective yield of the desired chloroalkoxysilane whether calculated on a molar basis or calculated per unit volume of the production equipment. Thus, a preferred embodiment of the invention is to conduct the process in the substantial absence of inert solvent. As used herein, in "substantial absence" means less than 5%, preferably less than 1%, and ideally no solvent whatsoever. As used here, the phrase "inert solvent" excludes the reactants and products of the desired hydrosilation. In the broadest practice of the invention, however, use of such solvents is optional and the noted disadvantage may be outweighed in certain cases for non-chemical reasons such as viscosity reduction of the reaction medium to promote rapid filtration, or for safety reasons including providing a heat sink.

It has surprisingly been found that the desired chloroorganosilanes can be prepared in accordance with the present invention using a hydromethoxysilane other than trimethoxysilane, such as methyldimethoxysilane, and using an allylic chloride other than allyl chloride, such as methallyl chloride, although the yield of the desired silane is somewhat lower.

Hydrosilation reaction conditions, such as temperature, pressure, time, and catalyst concentration, are not narrowly critical. One has a wide latitude in adjusting these factors to use various pieces of production equipment economically and safely. Such equipment will typically have provisions for heating, cooling, agitation, maintenance of inert atmospheres, and purification, as by filtration or distillation. Thus, equipment typically used in the prior art for large scale commercial hydrosilation reactions can be used for the process of the present invention, including equipment wherein allyl chloride is added to a refluxing, condensable stream of hydrosilicon compound in a zone containing a heterogeneous supported hydrosilation catalyst.

Preferred reaction conditions include a reaction temperature from about ambient temperature up to about 150° C. with 60° to 100° C. being most preferred. Generally, the process is performed at a pressure at or above atmospheric pressure with atmospheric pressure being most preferred. The reactants are charged at a cumulative mole ratio of hydromethoxysilane to allylic chloride between 1.01:1 and 3:1, with a range of 1.1:1 to 2:1 being preferred and 1.1:1 to 1.6:1 being most preferred. It is recognized that the process of the present invention may provide a high yield of the desired chloroalkylalkoxysilane in a truly batch system; however, the reaction must be conducted at a lower temperature, and reaction times are necessarily long. Thus, it is preferred to perform the hydrosilation at an elevated temperature by adding the allylic chloride to a molar excess of the hydromethoxysilane in the presence of the ruthenium metal-containing catalyst. One particular preferred mode of operation (semi-batch) involves slowly adding the full complement of allyl chloride over a period of time, to obtain a rate of addition of less than 3 moles of allylic chloride per hour per mole of hydromethoxysilane, to a reactor containing the full complement of the hydroalkoxysilane, for example, 1.15 to 1.6 molar equivalents of trimethoxysilane relative to the full amount of allyl chloride to be added. Preferably, the reactor contains 5 to 50 parts per million of ruthenium as $Ru_3(CO)_{12}$ by weight of total reactants and the reaction is conducted at 60°–100° C. Excess trimethoxysilane and the ruthenium catalyst can be recycled effectively to the next batch.

Since the process of the present invention is nearly quantitative with respect to the conversion of allylic chloride to the desired chloroalkylalkoxysilane product, particularly in the reaction of allyl chloride with trimethoxysilane, the generation of undesired by-products is greatly lowered. This reduces the amounts of materials to be destroyed or discarded as waste, to be isolated as separate streams, as by distillation, or to be vented from the reaction system. Since the process of the present invention is highly exothermic, external heating is not normally necessary, and reaction times are correspondingly shorter. Generally, the only impurities in significant amounts that need to be removed from the reaction product are the small excess of unreacted hydromethoxysilane and residual catalyst. These may be recycled to the next batch without purification. The low level of residual chloride that may be present in the product can be neutralized by methods well known in the art. Where the hydrosilation product of the present invention is used as an intermediate for the production of other organofunctional silicon compounds, its purity on initial synthesis may be sufficient that further purification, such as by distillation, may not be needed.

When applied to the preparation of chloropropyltrimethoxysilane, the process of the present invention provides a higher yield of the desired product, calculated on a molar basis from the limiting reactant, than any one-step or two-step process described in the prior art. The process also obtains such yields using significantly lower levels of ruthenium metal-containing catalyst than any process described in the art. The process also provides a higher yield per unit volume of equipment used, since use of inert solvents is obviated and significant quantities of waste by-products are not generated. The preferred order of combination of reactants in the present invention is in fact opposite to that employed to maximize the yield of chloropropyltrichlorosilane from one reported platinum-catalyzed reaction of trichlorosilane with allyl chloride. Moreover, the obtained yield is significantly higher than that reported for the platinum-catalyzed reaction of triethylsilane with allyl chloride, which is maximized by the addition of allyl chloride, necessarily containing trichlorosilane as a hydrosilation promoter, to the triethylsilane. The process of the present invention does not require the presence of a second hydrosilicon compound as a promoter.

The successful hydrosilation of methallyl chloride with trimethoxysilane or the hydrosilation of allyl chloride or methallyl chloride with other hydromethoxysilanes has not been described in the prior art.

While the process of the present invention does not require operation at a pressure above atmospheric pressure, an elevated pressure may be used, for example up to two atmospheres pressure, to control inadvertent potential emissions of allyl chloride to the environment by using a closed reactor. A pressure below atmospheric pressure may be used if a reaction temperature below the atmospheric pressure boiling point of the hydromethoxysilane is desired.

Allylic chloride reactants suitable for use in the present invention have the general formula $CH_2=CRCH_2Cl$ wherein R is H or a methyl group and thus may be selected from the group of allyl chloride and methallyl chloride. Allyl chloride is the preferred allylic chloride reactant.

Hydromethoxysilanes of the general formula $R'_x(R''O)_{3-x}SiH$ wherein $R'$ and $R''$ are methyl groups are suitable for use in the present invention and may be selected from the group of $(MeO)_3SiH$, $Me(MeO)_2SiH$, and $Me_2(MeO)SiH$, with $Me(MeO)_2SiH$ and $(MeO)_3SiH$ being preferred, and $(MeO)_3SiH$ being most preferred.

The ruthenium metal-containing catalyst must be present in the reaction medium and can be added in solution with the hydromethoxysilane, or with the allylic chloride, or both, or may be contained in heterogeneous form in a catalytic zone to which the reactants are introduced. A variety of homogeneous and heterogeneous forms of ruthenium metal-containing compounds may potentially be used as catalysts, and use levels (based on contained metal) are as low as those of commercially practiced platinum-catalyzed hydrosilation reactions. For example, ruthenium concentrations between about 2 and 300 ppm have proven to be suitable.

If oxygen is needed for catalyst activation, the amount of oxygen normally present in commercial raw materials, especially the reactants themselves, should generally be sufficient. This is particularly true for ruthenium carbonyl catalysts. If further catalyst activation is necessary, it can be accomplished simply by adding dilute oxygen, as for example, a mixture of 3% $O_2$ in $N_2$, to one or more of the reactants, or to the reaction medium to elevate the oxygen level encountered by the catalyst. Separate activation may more likely be required when the catalysts are ruthenium-phosphine complexes.

Suitable ruthenium-metal containing catalysts may be selected from homogeneous and heterogeneous ruthenium metal-containing compounds and complexes including the following: $Ru_3(CO)_{12}$; $[Ru(CO)_3Cl_2]_2$; Cyclooctadiene-$RuCl_2$; $RuCl_3$; $(Ph_3P)_2Ru(CO)_2Cl_2$; $(Ph_3P)_3Ru(CO)H_2$; Ru on Fe; Ru on $Al_2O_3$; Ru on Carbon; $Ru(AcAc)_3$; $RuBr_3$ and the like where Ph is a phenyl group and AcAc is an acetylacetonate group.

Ruthenium metal-containing compounds constituting ruthenium complexes containing only triphenylphosphine, hydrogen, and chlorine ligands such as $(Ph_3P)_3RuCl_2$, $(Ph_3P)_3RuHCl$, and $(Ph_3P)_3RuH_2$ are ineffective as catalysts for the reaction of trimethoxysilane with allyl chloride in the presence or absence of oxygen. This lack of catalytic activity is consistent with the results of prior investigators who examined the hydrosilation of allyl chloride with triethoxysilane. Where phosphine ligands are present, ligands other than or in addition to hydrogen or chlorine also should be present, such as a carbonyl or an olefin ligand, and a slightly higher level of activating oxygen may be needed.

The preferred ruthenium catalysts are the ruthenium carbonyl compounds, with $Ru_3(CO)_{12}$ and $[Ru(CO)_3Cl_2]_2$ being the most preferred. Catalyst from one batch can be recycled to the next batch without significant loss of activity. Catalyst use level may be in the range of 5.0 to 300 parts per million of contained Ru metal based on the total reactant charge, with 5 to 50 parts per million being preferred.

The products of the process of the present invention are chloroorganosilicon compounds of the general formula $R'_x(R''O)_{3-x}SiCH_2CHRCH_2Cl$ where x, R, R', and R'' are as previously defined. Preferred chloroalkylalkoxysilane products include: $(MeO)_3Si(CH_2)_3Cl$; $Me(MeO)_2Si(CH_2)_3Cl$; $Me_2(MeO)Si(CH_2)_3Cl$; $(MeO)_3SiCH_2CHMeCH_2Cl$; $Me(MeO)_2SiCH_2CHMeCH_2Cl$; and $Me_2(MeO)SiCH_2CHMeCH_2Cl$, where Me is a methyl group.

The more preferred products are $(MeO)_3Si(CH_2)_3Cl$, $Me(MeO)_2Si(CH_2)_3Cl$, $(MeO)_3SiCH_2CHMeCH_2Cl$, and $Me(MeO)_2SiCH_2CHMeCH_2Cl$, and the most preferred product is $(MeO)_3Si(CH_2)_3Cl$. The products of the process of the present invention may be purified by standard means, as by distillation, or where used as intermediates for a subsequent preparation, may be used directly without intermediate purification.

As noted above, the reaction also can be conducted in a continuous fashion by adding the hydromethoxysilane and allylic chloride reactants to the reactor at the desired molar excess of the silane. At steady state, the reactor will contain a sufficient excess of the hydromethoxysilane in admixture with product chloroalkylalkoxysilane to allow substantially quantitative yield of the desired product. The excess hydromethoxysilane can conveniently be recovered from the product stream and recycled.

Whereas the exact scope of the present invention is set forth in the appended claims, the following specific examples illustrate certain aspects of the present invention and, more particularly, point out the various aspects of the method for evaluating same. However, the examples are set forth for illustrative purposes only and are not to be construed as limitations on the present invention. The abbreviations g, ppm, equiv., GC, TMS, AC, and CPT respectively represent grams, parts per million, molar equivalent, gas chromatography, trimethoxysilane, allyl chloride, and 3-chloropropyltrimethoxysilane unless otherwise indicated; temperature is reported in degrees Centigrade. Yield percentages are determined by gas chromatography using an internal standard, except where yields are determined by actual weight, following vacuum distillation of the product. Unless stated otherwise, all reactions were run in standard laboratory glassware at atmospheric pressure under an inert atmosphere of nitrogen. In each example, product structures were identified by GC, GC/mass spectrometry, infrared spectroscopy, or nuclear magnetic resonance. Data from examples 1–26 are summarized in tabular form in Table 1.

EXAMPLE 1

REACTION OF TMS WITH AC

To a 500 ml four-necked flask fitted with septum, condenser, addition funnel, thermometer, magnetic stirrer, and heating mantle, were added 0.1338 g $Ru_{13}(CO)_{12}$ (319 ppm Ru metal by weight based on total reactant charge) and 128.8 g TMS (1.15 equiv. relative to AC). Heat was applied to elevate the temperature of the reactor contents to 80° C. and AC (70.4 g) was slowly added dropwise to the reactor over 1 hour. Due to the exothermic reaction, the temperature varied between 80°–96° C. After an additional 90 minutes at 80° C., analysis of the reaction medium by GC showed no residual AC (complete conversion of the limiting reactant) and an 88% yield of CPT, based on limiting allyl chloride reactant. Distillation at 89° C./18 mm provided 159.7 g of the chloroalkylalkoxysilane (CPT) product of 95% purity for a distilled yield of 83%. This example demonstrates obtaining a higher yield than prior art processes, which used a 4/1 mole ratio, while using only a 15% excess of hydrosilicon compound (1.15/1 mole ratio).

EXAMPLE 2

REACTION OF TMS WITH AC

The procedure of Example 1 was repeated with 0.0070 g $Ru_3(CO)_{12}$ (15 ppm Ru), 138.7 g TMS (1.15 equiv.) and 75.0 g AC, which was added dropwise over 1 hour at 79°–87° C. GC Analysis of the reaction medium 4 hours later showed no residual AC. To remove traces of chlorosilane by-products from the reaction mixture, anhydrous sodium bicarbonate (14.8 g) was added and stirred briefly. Vacuum distillation provided 136.6 g of CPT at 97% purity for a distilled yield of 73%. This example demonstrates yields equivalent to prior art processes using a catalyst concentration of only 15 ppm of Ru and only a 15% excess of hydrosilicon compound.

EXAMPLE 3

REACTION OF TMS WITH AC

The procedure of Example 1 was repeated on a smaller scale using a 250 ml flask as the reactor, 0.0249 g of $Ru_3(CO)_{12}$ (100 ppm of Ru), 90.1 g of TMS (2.0 equiv.), and 28.2 g of AC. The AC was added dropwise to the reactor containing the TMS over 30 minutes at 78°–98° C. GC Analysis of the reaction mixture after 90 additional minutes at 80° C. showed no residual AC (complete conversion), and a CPT yield of 97%. This example demonstrates a very high CPT yield using a 100% excess of hydrosilicon compound.

EXAMPLE 4

REACTION OF TMS WITH AC

The procedure of Example 3 was repeated using 0.0196 g of $RH^3(CO)_{12}$ (97 ppm of Ru), 69.0 g of TMS (1.60 equiv.), and 27.0 g of AC. The AC was added dropwise to the reactor of TMS over 20 minutes at 72°–88° C. GC Analysis of the reaction mixture after 70 additional minutes at 80° C. showed no residual AC, no chlorosilane derivative of CPT, and a 99% yield of CPT. Vacuum distillation at 83° C./13 mm provided 60.6 g of CPT product, for a distilled yield of 90%. This example demonstrates results essentially equivalent to Example 3 using only a 60% excess of hydrosilicon compound.

EXAMPLE 5

REACTION OF TMS WITH AC

The procedure of Example 3 was repeated with 0.0240 g of $Ru_3(CO)_{12}$ (109 ppm of Ru), 70.5 g of TMS (1.30 equiv.), and 33.8 g of AC. The AC was added dropwise to the reactor of TMS over 35 minutes at 80°–95° C. After 2 more hours at 80° C., GC analysis of the reaction mixture showed no residual AC and a CPT yield of 94%. This example demonstrates a very high CPT yield with only a 30% excess of hydrosilicon compound.

EXAMPLE 6

REACTION OF TMS WITH AC

The procedure of Example 4 was repeated on a larger scale using a 3 liter flask, and 0.0178 g of $Ru_3(CO)_{12}$ (15 ppm of Ru), 397.1 g of TMS (1.60 equiv.), and 155.5 g of AC. As before, the AC was added dropwise to the reactor of TMS over 35 minutes at 80°–96° C., followed by an additional 1 hour at 80° C. GC Analysis of the reaction mixture showed no residual AC and a CPT yield of 99%, with no contaminant chlorosilane derivative of CPT. Vacuum distillation at 108° C./38 mm provided 383.4 g of 97% pure product for a distilled yield of 92%. This example demonstrates that a very high yield of CPT can be obtained, in the absence of inert solvent, with only 15 ppm of ruthenium and a 60% excess of hydrosilicon compound.

EXAMPLE 7

REACTION OF TMS WITH AC

The procedure of Example 6 was repeated using the same apparatus and using the distillation residue from Example 6 as the sole catalyst source. TMS (394.1 g, 1.60 equiv.) was added to the flask and was heated to 80° C., followed by slow addition of 154.5 g of AC dropwise over 90 minutes at 80–87° C. Once the AC addition was complete, the reaction mixture was heated for an additional 2 hours at 80°–107° C. GC Analysis of the reaction mixture showed no residual AC. Vacuum distillation at 105° C/35 mm provided 350.2 g of 96% pure product for a distilled yield of 84%. This example demonstrates the possibility for recycling the ruthenium catalyst effectively even at a concentration of only 15 ppm.

EXAMPLE 8

REACTION OF TMS WITH AC

The procedure and equipment of Example 1 were used to react 118.3 g of 94% pure TMS, recovered from the reaction mixture of Example 6, and 43.6 g of AC, in the presence of 0.0059 g of $Ru_3(CO)_{12}$ (17 ppm of Ru). The AC was added dropwise to the reactor of TMS over 25 minutes at 79°–99° C., followed by heating the reaction mixture at 80° C. for 45 minutes. GC Analysis of the reaction mixture showed no residual AC and a CPT yield of 99%. Vacuum distillation at 105° C./40 mm provided 102.5 g of product for a distilled yield of 92%. This example demonstrates that excess TMS recovered and recycled from a prior run can be used effectively, in the absence of inert solvent, with only 17 ppm of Ru and only a 60% excess of the hydrosilicon compound to provide a very high yield of CPT.

EXAMPLE 9

REACTION OF TMS WITH AC

The procedure of Example 3 was repeated using AC, TMS (1.15 equiv.), $Ru_3(CO)_{12}$ at 247 ppm of Ru except that all of the reactants were combined at start and were heated with an oil bath maintained near 50° C. for 64 hours. A recording thermometer monitored the actual reaction temperature every 3 minutes. The temperature ranged from 52.6°–66.6° C. (average of 53.6° C. with a maximum of 66.6° C. at 171 minutes). GC Analysis of the reaction after 64 hours showed a CPT yield of 83%. This example demonstrates that good yields can be obtained even in a truly batch system at lower temperatures in the absence of inert solvent using only a 15% molar excess of the hydrosilicon compound at considerably longer reaction times.

EXAMPLE 10

REACTION OF TMS WITH AC

The procedure of Example 9 was repeated using AC, TMS (1.15 equiv.), and $Ru_3(CO)_{12}$ at 222 ppm of Ru. Again, all the reactants were combined at start and the reaction mixture was heated on an oil bath maintained at near 25° C. for 64 hours. The temperature of the reaction mixture ranged from 26.2°–27.7° C. over that time (average of 26.9° C. with a maximum of 27.7° C. at 3024 minutes). GC Analysis after 64 hours showed a CPT yield of 94%. Viewed in conjunction with Example 9, this example shows that overall yields and selectivities improve as the temperature is lowered, and that excellent yields can be obtained at long reaction times in the absence of inert solvent with only 15% excess hydrosilicon compound.

EXAMPLE 11

REACTION OF TMS WITH AC

The procedure of Example 3 was repeated using 0.0014 g of $Ru_3(CO)_{12}$ (6.1 ppm of Ru), 70.7 g of TMS (1.16 equiv.), and 38.2 g of AC. The AC was added slowly over 2 hours to the reactor of TMS, the temperature varying between 75°–92° C., followed by heating the reaction mixture at 80° C. for an additional 19 hours. GC Analysis of the reaction mixture showed no residual AC with a CPT yield of 86%. This example demonstrates that a good CPT yield can be obtained in the absence of inert solvent using less than 15 ppm of Ru catalyst at a somewhat longer reaction time.

EXAMPLE 12

REACTION OF TMS WITH AC

The procedure of Example 11 was followed using 0.0005 g of $Ru_3(CO)_{12}$ (2.2 ppm of Ru), 70.4 g of TMS (1.16 equiv.), and 38.2 g of AC. The AC was added dropwise over 2 hours to the reactor of TMS at 76°–82° C., followed by heating the reaction mixture at 80° C. for an additional 20 hours. GC Analysis of the reaction mixture showed some residual AC, with a CPT yield of only 58%. This example demonstrates that catalyst levels below those of Example 12 still provide a modest yield of CPT at a similarly long reaction time.

EXAMPLE 13

REACTION OF TMS WITH AC

The procedure of Example 11 was repeated using 2.34 g of a 51 ppm solution of $Ru_3(CO)_{12}$ in TMS (1.0 ppm of Ru relative to the total weight of reactants), 70.2 g of TMS (1.15 equiv.), and 38.2 g. of AC. The AC was added to the reactor containing TMS over 3 hours at 76°–82° C. followed by heating the reaction mixture at 80° C. for an additional 4 days. GC Analysis of the reaction mixture showed a considerable amount of residual AC and a CPT yield of only 37%.

EXAMPLE 14

REACTION OF TMS WITH AC

The procedure of Example 3 was repeated using 70.2 g of TMS (1.15 equiv.), 0.0276 g of $[RUCl_2(CO)_3]_2$ (101 ppm of Ru), and 38.1 g of AC. The AC was added dropwise to the reactor of TMS over 40 minutes at 77°–87° C., followed by heating the reaction mixture at 80° C. for an additional 17 hours. GC Analysis of the reaction mixture showed no residual AC and a CPT yield of 93%. This example demonstrates that another ruthenium metal-containing catalyst, $[RuCl_2(CO)_3]_2$, can be used in place of $Ru_3(CO)_{12}$.

EXAMPLE 15

REACTION OF METHYLDIMETHOXYSILANE WITH AC

The procedure of Example 3 was repeated using 30.8 g of methyldimethoxysilane (1.16 equiv.), 0.0028 g of $Ru_3(CO)_{12}$ (27 ppm of Ru), and 18.9 g of AC. The AC was added dropwise to the reactor of methyldimethoxysilane at reflux (59° C.) over 90 minutes, followed by heating the reaction mixture at 70° C. for an additional 2 hours. Vacuum distillation at 84° C./20 mm provided 30.3 g of 92% pure 3-chloropropylmethyldimethoxysilane (70% yield). This example demonstrates that methyldimethoxysilane can be used in place of TMS with no inert solvent and only 27 ppm of Ru to provide a good yield of the desired chloroalkylalkoxysilane product.

EXAMPLE 16

REACTION OF METHYLDIMETHOXYSILANE WITH METHALLYLCHLORIDE

The procedure of Example 3 was repeated using 30.1 g of methyldimethoxysilane (1.15 equiv.), 0.0030 g of $Ru_3(CO)_{12}$ (27 ppm of Ru), and 22.7 g of methallyl chloride (MAC). The MAC was added dropwise to the reactor containing the methyldimethoxysilane over 2 hours at 60° C., followed by heating the reaction mixture at 80° C. for 19 additional hours. Vacuum distillation at 5° C./22 mm provided 34.4 g (63% yield) of 3-chloro-2-methylpropylmethyldimethoxysilane. This example demonstrates that good yields are obtained when MAC is substituted for AC, and methyldimethoxysilane is substituted for TMS, in the absence of inert solvent and using only 27 ppm of Ru.

EXAMPLE 17

REACTION OF TMS WITH METHALLYL CHLORIDE

The procedure of Example 1 was repeated with 77.7 g of TMS (1.15 equiv.), 0.0266 g of $Ru_3(CO)_{12}$ (99 ppm of Ru), and 50.2 g of methallyl chloride (MAC). The MAC was added dropwise to the reactor of TMS over 3 hours at 78°–88° C., followed by heating the reaction mixture at 80° C. for 16 more hours. After cooling to room temperature, 5.7 g of sodium bicarbonate and 2.4 g of methanol were added to neutralize any silicon-bonded chloride. Vacuum distillation at 116° C./42 mm provided 80.6 g of 99% pure 3-chloro-2-methylpropyltrimethoxysilane (83% yield). This example demonstrates that MAC can be used in place of AC and provides a very good yield of the desired chloroalkylalkoxysilane in the absence of inert solvents.

EXAMPLE 18

CONTINUOUS REACTION OF TMS WITH AC

A hydrosilation reaction was run in a 250 ml 4-necked flask fitted with 2 addition funnels, a thermometer, a sparging tube, a heating mantle, and a magnetic stirrer. One addition funnel was charged with a solution of 0.1788 g of $Ru_3(CO)_{12}$ in 542 g of TMS (1.62 equiv.), and the other with allyl chloride. The flask was initially charged with 100 g of CPT and 0.0211 g of $Ru_3(CO)_{12}$. Prior to and during the reaction, the system was sparged gently with a mixture 3% $O_2$/97% $N_2$. The contents of the flask initially were heated to 80° C. and simultaneous addition was begun from both addition funnels. Crude reaction product was removed from the flask by a pump to maintain a constant level of reaction mixture in the flask. After 5 hours of operation, a total of 367.8 g of TMS had been added along with 141.8 g of AC. The reaction was then terminated. A total of 550.5 g of crude product was collected which contained 405.7 g of CPT by GC analysis. The yield of CPT was 83% based on the limiting AC charged to the flask, corrected for the 100 g of CPT :initially charged. This example demonstrates that the process of the present invention can be run in a continuous reactor.

EXAMPLE 19

REACTION OF TMS WITH AC

The procedure of Example 3 was modified with 21.8 g of AC, 0.0132 g of $Ru_3(CO)_{12}$ (101 ppm of Ru), and 40.3 g (1.16 equiv.) of TMS. The TMS was slowly added dropwise to the reactor containing the AC at reflux, beginning at 45° C., over 30 minutes, followed by heating the reaction mixture at 80° C. (with a brief exothermic excursion to 117° C.) for 4 more hours. GC Analysis of the reaction mixture showed no residual AC and a CPT yield of 67%. This example, in conjunction with Example 5, demonstrates that the preferred mode of combination is the addition of AC to a molar excess of TMS.

EXAMPLE 20

REACTION OF TMS WITH AC

The procedure of Example 19 was repeated with 22.2 g of AC, except that 0.0134 g of $Ru_3(CO)_{12}$ (102 ppm of Ru) was dissolved in 40.2 g (1.13 equiv.) of TMS. The TMS catalyst solution was added dropwise to the reactor of AC beginning at reflux (45° C.), followed by heating the reaction mixture at 80° C. (with a brief exothermic excursion to 112° C.) for 5 more hours. GC Analysis of the reaction mixture showed no residual AC and a CPT yield of 63%. This example, in conjunction with Examples 5 and 19, again demonstrates that the preferred mode of combination is addition of AC to a molar excess of TMS, regardless of whether the Ru catalyst is in the TMS or the AC.

EXAMPLE 21

REACTION OF TMS WITH AC

The procedure of Example 3 was repeated except that 25.1 g of TMS (1.13 equiv.), 13.9 g of AC, and 0.0084 g of $Ru_3(CO)_{12}$ (102 ppm of Ru) were combined in a reactor at room temperature and then heated to 80°–85° C. over 150 minutes. GC Analysis of the batch reaction mixture showed no residual. AC and a CPT yield of 68%.

EXAMPLE 22

REACTION OF TMS WITH AC

The procedure of Example 3 was repeated using 70.0 g of TMS (1.15 equiv.), 0.0230 g of $Ru_3(CO)_{12}$ (101 ppm of Ru), and 38.2 g of AC. The AC was added dropwise to the reactor of TMS at 80° C. over 45 minutes, followed by heating the reaction mixture at 70°–83° C. for 90 more minutes. The nitrogen atmosphere had been replaced by an air atmosphere for this example. GC Analysis of the reaction mixture showed no residual AC and a CPT yield of 77%. In view of Example 5, this example suggests that use of air in place of nitrogen has a negative effect on CPT yield.

EXAMPLE 23

REACTION OF TMS WITH AC

The procedure of Example 22 was repeated using 70.1 g of TMS (1.15 equiv.), 0.0231 g of $Ru_3(CO)_{12}$ (101 ppm of Ru), and 38.0 g of AC. The AC was added dropwise to the reactor of TMS at 80° C. over 30 minutes, followed by heating the reaction mixture at 76°–90° C. for 1 more hour. The air atmosphere was replaced with a gentle sparge through a subnatant tube with a 3% $O_2$/97% $N_2$ mixture throughout the run. GC Analysis of the reaction mixture showed no residual AC and a CPT yield of 83%. In view of Examples 5 and 22, this example suggests that an atmosphere containing 3% $O_2$ has a slightly negative effect on CPT yield when using a ruthenium carboxyl catalyst.

EXAMPLE 24

REACTION OF TMS WITH AC

The procedure of Example 23 was repeated, except that reactants and the reaction mixture were sparged gently through a subnatant tube with $N_2$ to remove dissolved $O_2$, using 70.1 g of TMS (1.15 equiv.), 0.0229 g of $Ru_3(CO)_{12}$ (100 ppm of Ru), and 38.0 g of AC. The AC was added dropwise to the TMS over 30 minutes at 80° C., followed by heating the reaction mixture at 75°–92° C. for 1 more hour. GC Analysis of the reaction mixture showed no residual AC and a CPT yield of 89%. Viewed in conjunction with Example 5, this example suggests that the levels of dissolved $O_2$ normally present in the TMS and AC raw materials do not have a negative effect on CPT yield, and that even lower levels do not have a significant effect on CPT yield.

EXAMPLE 25

REACTION OF TMS WITH AC

The batch procedure of Example 21 was repeated using a 50 ml flask, 6.6 g of TMS (1.16 equiv.), 3.5 g of AC, and 0.0073 g of $Ru_3(CO)_{12}$ (343 ppm of Ru). The mixture was warmed briefly, causing a short exotherm to 109° C., followed by heating the reaction mixture at 80° C. overnight. GC Analysis of the reaction mixture showed no residual AC and a 67% yield of CPT. This example, in conjunction with Examples 1 and 21, further demonstrates it is preferred, even with more than 300 ppm of Ru, to add AC to a molar excess of TMS.

EXAMPLE 26

REACTION OF TMS WITH AC

The procedure of Example 1 was followed using a 100 ml flask which was charged with 19.6 g of TMS (1.25 equiv.), 0.0049 g of $Ru_3(CO)_{12}$ (55 ppm of Ru), 12.8 g of toluene (30% by weight of total reactants) and 0.46 g of mesitylene (internal standard for GC analysis), and the reactor contents were heated to 80° C. AC (9.8 g) was slowly added dropwise over 2 hours to the reactor, followed by heating at 80° C. for three more hours. GC Analysis of the reaction mixture showed only a trace of unreacted AC and a CPT yield of 70%. However, the GC scan showed high selectivity to the desired product and a material balance of only 91.7%. These observations suggest that the yield was limited not by undesired side reactions but instead by escape of AC from the reactor due to both its low boiling point and the slow rate of reaction. On that basis, the yield based on converted AC was essentially quantitative. This example, in conjunction with subsequent Comparative Example B, shows that high yields can be obtained in the presence of at least some solvents if AC is slowly added to a molar excess of TMS.

EXAMPLE 27

CATALYST SCREENING, REACTION OF TMS WITH AC

A premix of TMS (1.15 equiv.) and AC was used in 5 g portions in 10 ml vials with 98–131 ppm of Ru as provided by a variety of ruthenium metal-containing catalysts, compounds and complexes. The vials were heated at 80° C. for 14 hours, and analyzed by GC using an internal standard. Under these conditions, which are not optimal, $Ru_3(CO)_{12}$ provided a CPT yield of only 51%. Positive yields were obtained for cis-dichloro-bis(2,2'-bipyridyl)Ru II, $RuBr_3$, $Ru(acetylacetonate)_3$, Ru on carbon, $[RuCl_2(CO)_3]_2$, (1,5-cyclo-octadiene)$RuCl_2$, $RuCl_3$, Ru on iron, Ru on alumina, $(Ph_3P)_2Ru(CO)_2Cl_2$, and $(Ph_3P)_3Ru(CO)H_2$. CPT yields of 0% were observed for $(Ph_3P)_3RuCl_2$, $(Ph_3P)_3RuCl_3$, $(Ph_3P)_3RuH_2$, and $(Ph_3P)_3RuHCl$. This example demonstrates that while a variety of ruthenium metal-containing compounds are catalysts for the process of the present invention, phosphine complexes of ruthenium which contain only hydrogen and chlorine as additional ligands are not.

TABLE 1

| Example No. | AlkoxySilane (AS) | Olefin (O) | Mole Ratio (AS/O) | Catalyst Type | Catalyst Conc. (ppm) | Temperature Range (°C.) | Total Reaction Time (hrs.) | Yield (%) |
|---|---|---|---|---|---|---|---|---|
| 1 | TMS | AC | 1.15 | A | 319 | 80–96 | 2.5 | 88 |
| 2 | TMS | AC | 1.15 | A | 15 | 79–87 | 5 | 73* |
| 3 | TMS | AC | 2.0 | A | 100 | 78–98 | 2 | 97 |
| 4 | TMS | AC | 1.6 | A | 97 | 72–88 | 1.5 | 99 |
| 5 | TMS | AC | 1.3 | A | 109 | 80–95 | 2.5 | 94 |
| 6 | TMS | AC | 1.6 | A | 15 | 80–96 | 1.5 | 99 |
| 7 | TMS | AC | 1.6 | A+ | — | 80–87 | 3.5 | 84* |
| 8 | TMS# | AC | — | A | 17 | 79–99 | 1.1 | 99 |
| 9 | TMS | AC | 1.15 | A | 247 | 50–67 | 64 | 83 |
| 10 | TMS | AC | 1.15 | A | 222 | 25–28 | 64 | 94 |
| 11 | TMS | AC | 1.16 | A | 6.1 | 75–92 | 21 | 86 |
| 12 | TMS | AC | 1.16 | A | 2.2 | 76–82 | 22 | 58 |
| 13 | TMS | AC | 1.15 | B | 1.0 | 76–82 | 99 | 37 |
| 14 | TMS | AC | 1.15 | C | 101 | 77–87 | 17.7 | 93 |
| 15 | MeDMeOS | AC | 1.16 | A | 27 | 59–70 | 3.5 | 70* |
| 16 | MeDMeOS | MAC | 1.15 | A | 27 | 60–80 | 21 | 63 |
| 17 | TMS | MAC | 1.15 | A | 99 | 78–88 | 19 | 83* |
| 18 | TMS | AC | 1.62 | A | — | 80 | — | 83 |
| 19 | TMS | AC | 1.16 | A | 101 | 45–80 | 4.5 | 67 |
| 20 | TMS | AC | 1.13 | A | 102 | 45–80 | 5 | 63 |
| 21 | TMS | AC | 1.13 | A | 102 | 80–85 | 2.5 | 68 |
| 22 | TMS | AC | 1.15 | A | 101 | 70–80 | 2.25 | 77 |
| 23 | TMS | AC | 1.15 | A | 101 | 76–90 | 1.5 | 83 |
| 24 | TMS | AC | 1.15 | A | 100 | 75–92 | 1.5 | 89 |
| 25 | TMS | AC | 1.16 | A | 343 | 80 | — | 67 |
| 26 | TMS | AC | 1.25 | A | 55 | 80 | 3 | 70 |

*Yield after distillative purification.
+Recycled Catalyst A.
Recycled TMS.
TMS = Trimethoxysilane
MeDMeOS = Methyldimethoxysilane
AC = Allyl Chloride
MAC = Methyally Chloride
Catalyst A = $Ru_3(CO)_{12}$
Catalyst B = Ru solution in TMS
Catalyst C = $[RuCl_2(CO)_3]_2$

Comparative Example A

Solvent Screening, Reaction of TMS with AC

The procedure of Example 26 was repeated using a premix of TMS (1.16 equiv.) and AC in 2.48–2.94 g portions of premix in 10 ml vials with 0.0011–0.0014 g of $Ru_3(CO)_{12}$ (100–123 ppm of Ru) and 2.45–2.67 g portions of various solvents (hexane, acetonitrile, isopropyl ether, 1,2-dichloroethane, acetone, and toluene). The vials were heated at 70° C. for 17 hours and analyzed by GC using an internal standard. A control vial with no solvent showed a 47% CPT yield under these non-optimal conditions; all runs with solvent provided lower yields, including 0% yields with acetone and acetonitrile. This example demonstrates that higher yields are obtained in the absence of inert solvent.

Comparative Example B

Toluene Solvent, Reaction of TMS with AC

Several batch reactions were run with all reactants combined at the start using TMS (1.00–1.25 equiv.), AC, $Ru_3(CO)_{12}$ (105–958 ppm of Ru), and 30–60% by weight of toluene solvent, at 80° C. for 15–17 hours in glassware, with one run at 120° C. for 2 hours in an autoclave. GC Analysis showed the highest yield to be 58% at the highest TMS/AC ratio (1.25 equiv.) and the lowest toluene content (30% by weight). This example, in conjunction with Comparative Example A and Example 26, demonstrates that highest yields are obtained in the absence of inert solvent unless, if a solvent is present, AC is added to a molar excess of TMS.

What is claimed is:

1. A method for preparing a chloroalkylalkoxysilane comprising reacting an allylic chloride with a molar excess of a hydromethoxysilane in a reaction vessel in the presence of an effective amount of a ruthenium metal-containing catalyst, and in substantial absence of an inert solvent with the proviso that when the ruthenium metal-containing catalyst is a phosphine complex, the catalyst must contain an additional ligand other than hydrogen and chlorine.

2. The method of claim 1 wherein the chloroalkylalkoxysilane has the formula $R'_x(R''O)_{3-x}SiCH_2CHRCH_2Cl$, the allylic chloride has the formula $CH_2=CRCH_2Cl$, and the hydromethoxysilane has the formula $R'_x(R''O)_{3-x}SiH$, wherein x is 0, 1, or 2, R is H or a methyl group, R' is a methyl group, and R" is R'.

3. The method of claim 1 wherein the ratio of hydromethoxysilane to allylic chloride ranges from 1.01 to 3.0 on a molar basis, the effective amount of ruthenium metal-containing catalyst ranges from 2.0 to 300 parts per million of ruthenium by weight of total reactants, and said reacting is conducted at a temperature in the range of from ambient temperature to 150° C.

4. The method of claim 3 wherein said allylic chloride and hydromethoxysilane are combined in said reaction vessel before said reacting and said reacting is conducted at a temperature in the range of from ambient temperature to 70° C.

5. The method of claim 1 wherein the allylic chloride is selected from the group consisting of $CH_2=CHCH_2Cl$ and $CH_2=CMeCH_2Cl$, the hydromethoxysilane is selected from the group consisting of $(MeO)_3SiH$, $Me(MeO)_2SiH$, and $Me_2(MeO)SiH$, and the ruthenium metal-containing catalyst is selected from the group consisting of $Ru_3(CO)_{12}$, and $[RuCl_2(CO)_3]_2$.

6. The method of claim 1 wherein said reacting is conducted by adding said allylic chloride to said reaction vessel containing said excess of hydromethoxysilane.

7. The method of claim 3 wherein the allylic chloride is $CH_2=CHCH_2Cl$, the hydromethoxysilane is $(MeO)_3SiH$ in an amount to provide a molar ratio of 1.15 to 1.6 relative to the allylic chloride, the ruthenium metal-containing catalyst is $Ru_3(CO)_{12}$ in an amount to provide 5 to 50 parts per million of contained Ru metal by weight, the reacting temperature ranges from 60° to 100° C., and the allylic chloride is added to said reacting vessel containing said molar excess of hydromethoxysilane.

8. A method for preparing a chloroalkylalkoxysilane which comprises adding an allylic chloride to a reaction vessel containing a molar excess of hydromethoxysilane in the presence of an effective amount of a ruthenium metal-containing catalyst, with the proviso that when the ruthenium metal-containing catalyst is a phosphine complex, the catalyst must contain an additional ligand other than hydrogen and chlorine.

9. The method of claim 8 wherein the chloroalkylalkoxysilane has the formula $R'_x(R''O)_{3-x}SiCH_2CHRCH_2Cl$, the allylic chloride has the formula $CH_2=CRCH_2Cl$, and the hydromethoxysilane has the formula $R'_x(R''O)_{3-x}SiH$, wherein x is 0, 1, or 2, R is H or a methyl group, R' is a methyl group, and R" is R'.

10. A method for preparing a chloroalkylalkoxysilane which comprises adding an allylic chloride and a hydromethoxysilane continuously to a reaction vessel at a molar ratio of hydromethoxysilane to allylic chloride in the range of 1.01 to 3.0, reacting said allylic chloride and hydromethoxysilane in said reaction vessel in the presence of an effective amount of a ruthenium metal-containing catalyst, and in substantial absence of an inert solvent, with the proviso that when the ruthenium metal-containing catalyst is a phosphine complex, the catalyst must contain an additional ligand other than hydrogen and chlorine, and recovering said chloroalkylalkoxysilane from said reaction vessel.

11. The method of claim 7 wherein said reacting is conducted at atmospheric pressure.

12. The method of claim 8 wherein the ruthenium metal-containing catalyst is selected from the group consisting of $Ru_3(CO)_{12}$ and $[RuCl_2(CO)_{32}$.

13. The method of claim 9 wherein the ruthenium metal-containing catalyst is selected from the group consisting of $Ru_3(CO)_{12}$ and $[RuCl_2(CO)_3]_2$.

14. The method of claim 10 wherein the ruthenium metal-containing catalyst is selected from the group consisting of $Ru_3(CO)_{12}$ and $[RuCl_2(CO)_3]_2$.

15. The method of claim 1 wherein the reacting is conducted for 1 to 15 hours.

16. The method of claim 15 wherein the effective amount of ruthenium metal-containing catalyst ranges from 5 to 300 parts per million of ruthenium by weight of total reactants.

17. The method of claim 16 wherein the reacting is conducted at atmospheric pressure and at a temperature in the range of 60° to 100° C.

18. The method of claim 17 wherein the hydromethoxysilane and allylic chloride are reacted at a cumulative mole ratio of hydromethoxysilane to allylic chloride between 1.01:1 and 3:1.

19. The method of claim 11 wherein the ruthenium metal-containing catalyst and the hydromethoxysilane are combined and heated to the reacting temperature prior to addition of the allylic chloride.

20. The method of claim 15 wherein the ruthenium metal-containing catalyst comprises its mixture with said chloroalkylalkoxysilane.

21. The method of claim 1 wherein a portion of at least one of said hydromethoxysilane and said ruthenium metal-containing catalyst are recovered from a prior reaction.

22. The method of claim 1 wherein the reaction vessel contents are sparged with an unreactive gas.

23. The method of claim 22 wherein the unreactive gas is selected from nitrogen and mixtures of nitrogen with minor amounts of oxygen.

24. A method of preparing a chloroalkylalkoxysilane comprising reacting an allylic chloride with a molar excess of a hydromethoxysilane in a closed reaction vessel at an elevated pressure in the presence of an effective amount of a ruthenium metal-containing catalyst, and in the substantial absence of an inert solvent with the proviso that when the ruthenium metal-containing catalyst is a phosphine complex, the catalyst must contain an additional ligand other than hydrogen and chlorine.

25. The method of claim 1 wherein the ruthenium metal-containing catalyst is a ruthenium halide.

26. The method of claim 24 wherein the ruthenium metal-containing catalyst is a ruthenium halide.

27. The method of claim 25 wherein the ruthenium halide is selected from the group consisting of ruthenium chloride and ruthenium bromide.

28. The method of claim 26 wherein the ruthenium halide is selected from the group consisting of ruthenium chloride and ruthenium bromide.

29. The method of claim 1 wherein the ruthenium metal-containing catalyst is a ruthenium halide hydrocarbon complex.

30. The method of claim 24 wherein the ruthenium metal-containing catalyst is a ruthenium halide hydrocarbon complex.

31. The method of claim 29 wherein the ruthenium metal-containing catalyst is (1,5-cyclooctadiene)$RuCl_2$.

32. The method of claim 30 wherein the ruthenium metal-containing catalyst is (1,5-cyclooctadiene)$RuCl_2$.

33. The method of claim 1 wherein the ruthenium metal-containing catalyst is ruthenium metal on a solid support.

34. The method of claim 24 wherein the ruthenium metal-containing catalyst is ruthenium metal on a solid support.

35. The method of claim 33 wherein the solid support is selected from the group consisting of iron, carbon and alumina.

36. The method of claim 34 wherein the solid support is selected from the group consisting of iron, carbon and alumina.

37. The method of claim 1 wherein the ruthenium metal-containing catalyst is selected from the group consisting of cis-dichloro-bis(2,2'-bipyridyl)Ru II and Ru(acetylacetonate)$_3$.

38. The method of claim 24 wherein the ruthenium metal-containing catalyst is selected from the group consisting of cis-dichloro-bis(2,2'-bipyridyl)Ru II and Ru(acetylacetonate)$_3$.

* * * * *